United States Patent [19]

Kulle et al.

[11] 4,406,440

[45] Sep. 27, 1983

[54] FLOW REGULATING DEVICE

[75] Inventors: Lee K. Kulle, Mundelien; John M. Hess, Streamwood, both of Ill.; James W. Scott, Mario, Iowa

[73] Assignee: Baxter Travenol Laboratories, Inc., Deerfield, Ill.

[21] Appl. No.: 302,573

[22] Filed: Sep. 15, 1981

Related U.S. Application Data

[63] Continuation of Ser. No. 133,677, Mar. 25, 1980, abandoned.

[51] Int. Cl.³ .............................................. F16L 55/14
[52] U.S. Cl. ..................................................... 251/6
[58] Field of Search ........................... 251/4, 5, 6, 367

[56] References Cited

U.S. PATENT DOCUMENTS

| | | |
|---|---|---|
| 1,330,523 | 2/1920 | Evitts et al. |
| 1,959,074 | 5/1934 | Bloxsom |
| 2,595,511 | 5/1952 | Butler |
| 2,615,668 | 10/1952 | Ernest |
| 2,693,765 | 11/1952 | Petri |
| 3,099,429 | 7/1963 | Broman |
| 3,102,710 | 9/1963 | Dresden |
| 3,135,259 | 6/1964 | Evans |
| 3,189,038 | 6/1965 | Von Pechmann |
| 3,215,395 | 11/1965 | Gorbar |
| 3,297,558 | 1/1967 | Hillquist |
| 3,497,175 | 2/1970 | Koland |
| 3,511,240 | 5/1970 | Williams et al. |
| 3,512,748 | 5/1970 | Wilson |
| 3,533,439 | 10/1970 | Hall |
| 3,625,472 | 12/1971 | Rychlik |
| 3,630,481 | 12/1971 | McGay |
| 3,685,787 | 8/1972 | Adelberg |
| 3,805,830 | 4/1974 | Smith |
| 3,893,468 | 7/1975 | McPhee |
| 3,900,184 | 8/1975 | Burke et al. |
| 3,915,167 | 10/1975 | Waterman |
| 3,918,675 | 11/1975 | Forberg |
| 3,948,477 | 4/1976 | Lample |
| 3,960,149 | 6/1976 | Bujan |
| 3,989,058 | 11/1976 | Jackson et al. |
| 4,013,263 | 3/1977 | Adelberg |
| 4,034,773 | 7/1977 | Huggins |
| 4,047,694 | 9/1977 | Adelberg |
| 4,238,108 | 12/1980 | Muetterties |
| 4,265,425 | 5/1981 | Morin |
| 4,307,868 | 12/1981 | Morin |

FOREIGN PATENT DOCUMENTS

| | | |
|---|---|---|
| 2043551 | 3/1979 | Fed. Rep. of Germany |
| 108209 | 9/1964 | Spain |

OTHER PUBLICATIONS

Literature from Cutter Laboratories, Inc. pertaining to a "Dependable Rate I.V. Set".

Primary Examiner—Alan Cohan
Assistant Examiner—Sheri M. Novack
Attorney, Agent, or Firm—John P. Kirby, Jr.; Garrettson Ellis; Bradford R. L. Price

[57] ABSTRACT

A flow regulating device and specifically an improved roller clamp with a length of conduit exhibiting low compression set properties disposed therein. The clamp includes an elongated box-like body having a fluid inlet at one end with a fluid outlet at the opposite end which are joined by the conduit to provide a flow lumen through the clamp. The roller is captured within a track in the body to selectively compress or release the conduit towards or away from a compression surface disposed at an angular variance to the track. The flow rate is regulated by appropriately positioning the roller. The conduit is captured within the body so as to be unaffected by external pulling or tugging forces.

5 Claims, 4 Drawing Figures

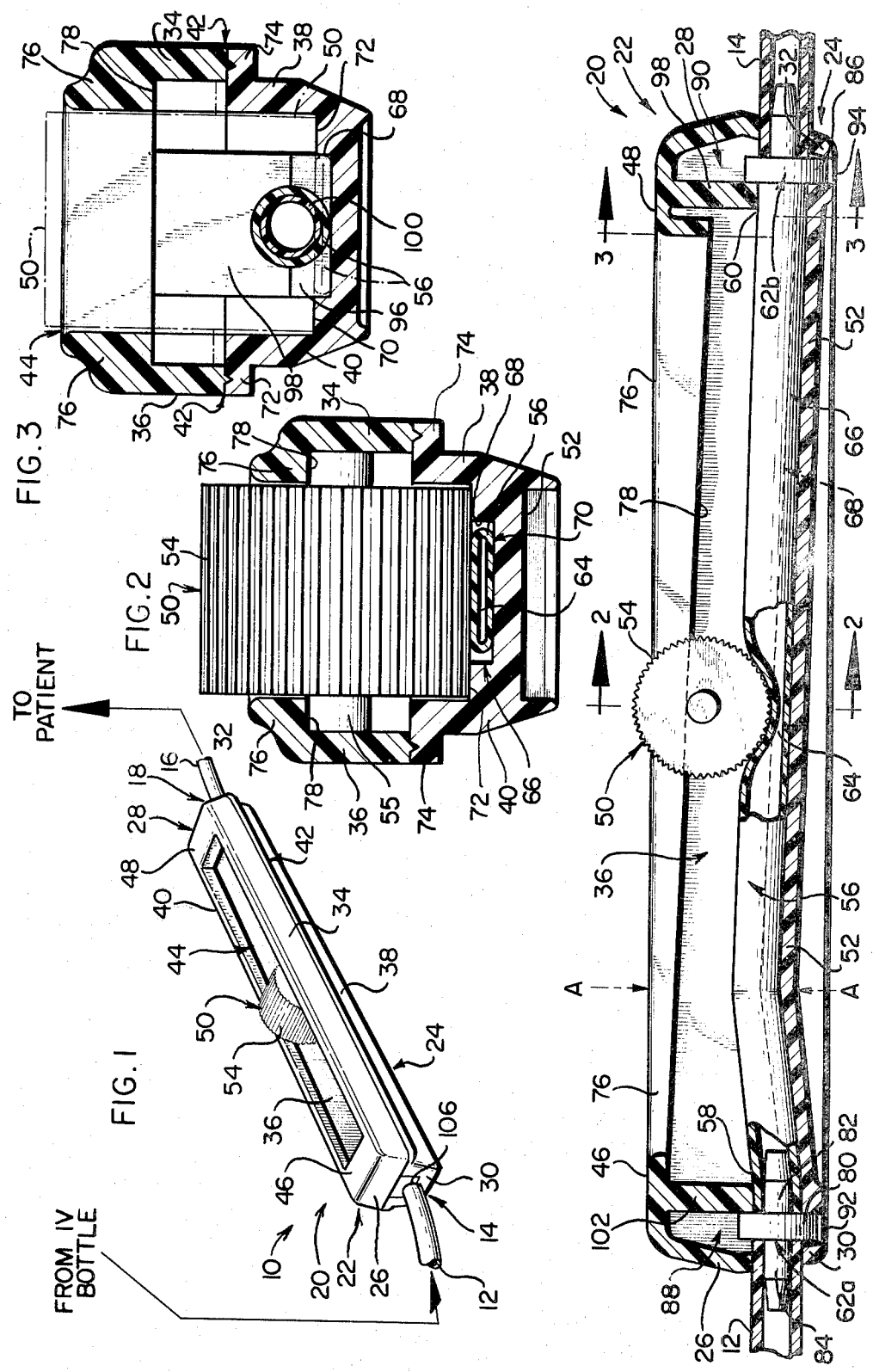

FLOW REGULATING DEVICE

CROSS-REFERENCE TO RELATED APPLICATION

This application is a continuation of U.S. Application Ser. No. 133,677, filed Mar. 25, 1980 now abandoned.

BACKGROUND OF THE INVENTION

This invention relates generally to clamps for use in regulating fluid flow rate through plastic tubing and more specifically to a self-contained device for regulating the fluid flow therethrough.

Plastic tubing, generally of a PVC, or vinyl material is extensively employed in hospitals as a fluid conduit in numerous applications. Vinyl tubing is inexpensive and generally inert so as to be advantageous for administering fluids to a patient such as in parenteral solution administration sets. Numerous devices such as cam, screw and roller type clamps are available for regulating the fluid flow rate of the solution reaching the patient by selectively compressing the tubing to vary the size of the fluid lumen. These flow regulating devices are positioned along the length of tubing to permit the operator to regulate the flow rate and the volume per unit time of liquid administered to a particular patient.

When vinyl tubing is compressed, its inherent rigidity produces a high internal strain to resist compression for the first several minutes after being clamped. Eventually, the tubing will begin to relieve its internal strain or undergo the phenomena of "cold flow" causing a progressive change in the cross-sectional area of the constricted tubing producing a potentially dangerous fluctuation in the desired flow rate. Consequently, these prior devices must be frequently monitored and re-adjusted to maintain a prescribed flow rate.

Although all of the types of clamps referred to above regulate flow by compressing the tubing, they are entirely dissimilar in operation and effectiveness. Cam-type clamps generally employ a transaxial cam to compress a particular transverse section of tubing, but are generally difficult for the attendent or nurse to manipulate and their configurations do not readily lend themselves to variable settings of flow regulation. Screw clamps have a threaded plunger to selectively compress the tubing beneath the plunger by which to regulate flow. However, screw clamps are notoriously unreliable in maintaining a set flow rate due to the formation of secondary lumens around the plunger caused by cold flow. Generally, the plunger cannot completely crimp the tubing closed to block flow for any length of time due to the increased tendency for the formation of secondary lumens on either side of the plunger.

Roller clamps have heretofore generally had a U-shaped body to fit over the tubing with a roller mounted therein to selectively compress the tubing against the base of the body. The early roller clamps, such as shown in U.S. Pat. No. 3,189,038, suffered a severe drawback from cold flow by providing a flat-inclined clamping surface relative to the movement of the roller to progressively compress the tubing in a uniform transverse cross-section against the compression surface which lead to secondary lumen formation.

In an attempt to overcome the difficulties with cold flow produced by a flat compression surface several roller clamps have been proposed with a grooved clamping surface. One such clamp compresses the transverse edges of the tubing by a roller mounted uniformly above a compression surface which has a channel of varying cross-section to control the lumen size. For example, U.S. Pat. No. 3,685,787 discloses a clamp having a roller spaced uniformly above a compression surface to squeeze the transverse edges of the tubing while permitting the central portion of the tube to flow into a longitudinal channel in the compression surface to form a lumen. The channel varies in depth from large to small to regulate lumen size. Although that device was an improvement over earlier roller clamps, the configuration and cross-sectional area of the channel still permitted "cold flow" migration of the compressed tubing wall into the excess channel space causing fluctuations in the desired flow rate. U.S. Pat. Nos. 4,031,263 and 4,047,694 disclose improvements to the embodiment of the 3,685,787 patent in an attempt to direct the cold flow away from the excess space in the channel and a recessed roller to permit migration of the tubing during cold flow into this additional space and away from flow-rate defining lumen. However, these and the other prior art roller clamps have not adequately overcome the disadvantages attributed to cold flow making the currently available roller clamps less than satisfactory.

To overcome some of these difficulties, the use of a cam-type clamp with an expensive and complicated multi-lumen insert of resilient material which does not exhibit the phenomena of cold flow when compressed, has been suggested in U.S. Pat. No. 3,805,830 to alleviate flow rate fluctuations attributed to cold flow and capillary action encountered with standard vinyl tubing. The patentee of U.S. Pat. No. 3,948,977 has proposed that the multi-lumen insert described therein may be employed with the screw clamp disclosed in U.S. Pat. No. 3,805,830. This screw clamp device suffers from the disadvantages of limited control range and difficulty of complete shut-off inherent with that type of clamp. Both of these clamps employing the resilient insert are subject to flow rate variations produced by tugging or stretching of the administration tubing by external forces. For example, movement by the patient which produced a pulling force would tend to change the flow rate due to the resilient, easily stretched insert making these devices unreliable for maintaining consistent flow rates.

Heretofore, the prior tubing clamps have failed to overcome flow rate fluctuations attributed to cold flow and/or external stretching forces causing them to be unsatisfactorily unreliable for failing to maintain a prescribed flow rate.

OBJECTS OF THE INVENTION

A primary object of the present invention is to provide an adjustable flow regulating device over an expanded control range which eliminates fluctuations from a desired flow rate setting by eliminating the phenomena of cold flow and preventing flow variations attributed to external forces.

A further object of the present flow regulating invention is to provide an improved roller clamp having a self-contained fluid conduit of material exhibiting small compression set properties constrained therein providing a clamp which is readily adaptable for use with conventional vinyl tubing administration sets.

SUMMARY OF THE INVENTION

A fluid regulating device and particularly an improved roller clamp, fluid regulating device is disclosed which provides a solution to the recurring problems of accurately regulating flow rate through plastic tubing attributed to cold flow and external stretching forces.

The present invention provides a roller clamp having an elongated two piece, box-like body provided with a fluid inlet at one end and a fluid outlet at the opposite end. A cylindrical roller is mounted within a track in the body for longitudinal movement. A length of conduit having low compression set characteristics is disposed between the bottom of the roller and a compression surface in the base providing a fluid passageway through the interior of the body from the inlet to the outlet. The compression surface has a minimal angular variance to the path of the roller. The flow rate through the conduit is regulated by longitudinally moving the roller along the length of the body which varies the area between the roller and compression surface to permit the conduit to be fully open at one end of the clamp and fully closed at the other end of the clamp.

The conduit is captured within the body and preferably, is captured in a slightly stretched configuration between the fluid inlet and the fluid outlet. In use, the present invention is readily adapted to receive a length of conventional plastic tubing leading from a source of fluid at the fluid inlet and to receive a length of conventional tubing at its fluid outlet. The elongated body provides an improved control range to permit slight adjustments in the flow lumen size of the conduit, which when set, will not vary due to cold flow nor be affected by external forces.

DESCRIPTION OF THE DRAWINGS

FIG. 1 is a perspective view of the roller clamp of this invention shown in use with a schematic representation of a conventional fluid administration set.

FIG. 2 is a vertical cross-sectional view of the roller clamp taken along lines 2—2 of FIG. 4.

FIG. 3 is a vertical cross-sectional view of the clamp taken along lines 3—3 of FIG. 4.

FIG. 4 is a longitudinal cross-sectional view, partially broken away of the clamp illustrated in FIG. 1.

DETAILED DESCRIPTION OF THE PREFERRED EMBODIMENTS

Referring to FIG. 1, a roller clamp 10 embodying various aspects of the present invention is shown in operative association with a conventional fluid solution administration set. A length of conventional flexible tubing 12, such as PVC or vinyl tubing, connects a source of fluid to a fluid inlet end 14 of the clamp 10 and another length of conventional tubing 16 is joined to a fluid outlet 18 and is suitably joined to the patient. In the illustrated embodiment of our flow regulating invention shown generally in FIGS. 1-4 an elongated box-like body 20 is longitudinally divided to provide two pieces shown generally as an upper member 22 and a lower member 24. The upper 22 and lower 24 members each include two end walls 26, 28 and 30, 32 and longitudinal side walls 34, 36 and 38, 40 which are cooperatively joined at juncture 42. The upper member 22 of the body 20 further includes an elongated opening 49 boardered at both ends by horizontal top walls 46 and 48 to provide a passageway and ready access to a roller 50, the box-like body 20 is cooperatively joined by any suitable means at the juncture 42. The roller 50 and upper 22 and lower 24 members are preferably molded from an essentially rigid plastic material to maintain close tolerances in the finished clamp.

Referring to FIGS. 2 and 4, the roller 50 is formed with a circumferential outer surface 54, which is preferably knurled as shown, with a centrally disposed axle 55. It will be understood that the roller 50 will generally be of a unitary construction and may include hub-like projections to serve as the axle 55.

Referring now to FIGS. 4 and 2, a length of conduit 56 is disposed within the body 20 and is connected at one end 58 to a means for defining a fluid inlet such as a nipple 62a, and with the other end 60 connected to a means for defining a fluid outlet, or a second nipple 62b. The conduit 56 provides a flow lumen 64 for defining a fluid passageway between the inlet 14 and outlet 18 ends of the clamp 10. Any suitable inert material exhibiting low compression set properties, such as silicone or latex, may be employed for the conduit 56 which virtually eliminates the problems attributed to cold flow. Preferably, the conduit 56 is an elastic silicone conduit, which is substantially inert to chemical leaching.

As shown in the orientations of FIGS. 2 and 4, the base wall 52 is provided with a conduit receiving channel 66. As shown, the channel 66 is defined by an elongated compression surface 70 joined by vertical shoulders 68 to roller bearing surfaces or ledges 72 projecting towards the center of the body 20 along the length of both walls 38 and 40. As shown in FIG. 2, the compression surface 70 of the channel 66 is suitably dimensioned to receive the conduit 56.

Referring to FIGS. 2 and 3, the lower member 24 of the body 20 is provided with horizontal walls 74 projecting outwardly which are suitably joined at the juncture 42 with the vertical sidewalls 34 and 36 of the upper member 22 of the body 20. The sidewalls 34 and 36 are provided with inwardly projecting horizontal lips 76 boardering the length of the passageway 44 to the top walls 46 and 48. As shown, the lower portion of the lips 76 are provided with flat hub bearing surfaces 78 which extend substantially along the longitudinal length of the body 20.

Turning momentarily to FIG. 4, the ledges 72 are spaced uniformly below the hub bearing surfaces 78 along the length of the body 20 beginning at a point A near the inlet end 14, to the outlet end 18 of clamp 10. As shown in FIGS. 2, 3 and 4, the roller 50 is appropriately dimensioned and mounted within a longitudinal track in the body 20 defined by ledges 72 and surfaces 76. Beginning at point A of the body 20, the uniform vertical distance between the hub bearing surfaces 78 and the ledges 72 is slightly less than the distance between the uppermost point of the axle 55 and the lowermost outer surface 54 of the roller 50 to create a slightly biased fit, but still permitting longitudinal movement of the roller 50 within the track.

As shown generally, the outer surface 54 of the roller 50 diametrically projects through the passageway 44 and compresses the conduit 56 towards the surface 70 of the channel 66.

Starting near the inlet end 18 of the clamp 10 indicated by A, the compression surface 70 is angled to converge toward the plane of the ledges 72 by providing a decreasing height of the shoulders 68 as the roller is moved longitudinally toward the fluid outlet end 18 of the body 20. Longitudinal movement of the roller 50 toward the outlet end 18 selectively compresses the conduit 56 toward the surface 70 to vary the size of the lumen 64 from a fully open position near the inlet end 14 to a fully closed position at the opposite end of the body as shown in FIG. 4. Alternately, opposite movement of the roller 50 opens the lumen 64 as a result of the low compression set properties of conduit 56. The base wall 52 and channel 66 slightly diverges away from the surfaces 78 to insure a completely open position when the roller 50 is positioned near the inlet end 14 of the clamp 10 as shown.

Referring now to FIG. 4, the nipple 62a is provided with a centrally disposed retainer ring 80 of larger diameter separating an inner tubular coupling 82 from an outer tubular coupling 84. As shown, the couplings 82 and 84 are preferably provided with tapered ends permitting ease of insertion of the conduit 56 to coupling 82 and the conventional vinyl tubing 12 to the coupling 84. The nipple 62b is similar in configuration and dimension to nipple 62a and is also provided with couplings to receive the conduit 56 and the conventional tubing 18 having a retaining ring 86 therebetween. As shown, the couplings of nipples 62a and 62b are dimensioned to be snugly received within the interior diameter of the inlet 12 and outlet 18 tubing and the conduit 56. Other embodiments for the nipples not shown, may be provided with variable sized couplings on either side of suitable clips or retainer rings and do not necessarily have to be identical.

As shown in FIG. 4, the retainer rings 80 and 82 of the nipples 62a and 62b are captured within similarly configured retaining spaces 88 and 90. The lower member 24 of the body 20 is provided with notches 92 and 94 for receiving the retainer rings 80 and 86 respectively. The space 90 is defined on the side towards the interior of the body 20 by a vertical lower yoke 96 upwardly extending from the lower member 24 and a downwardly projecting upper yoke 98 shown in FIG. 3. As shown in FIG. 4, the exterior side of space 90 is defined by the end wall 32 of the lower member 24 cooperatively joined with the end wall 28 of the upper member 22. FIG. 3 illustrates the co-action of the lower yoke 96 with the upper yoke 98 to circumferentially collar the retainer rings 80 and 86. Preferably, the lower 96 and upper 98 yokes are suitably dimensioned to avoid snugly compressing the conduit 56 against the inner coupling 100 of nipple 62b. In the preferred dimensions of the yokes, the possibility of leakage due to slight manufacturing variations causing an uneven compression by the yokes is avoided. If desired, a suitable binder material may be provided to glue the conduit 56 to the nipples to insure leakproof integrity. As illustrated in FIGS. 1 and 4, the space 88 is similar defined by an upper yoke 102, a lower yoke (not shown) and by the end wall 26 of the upper member 22 and end wall 30 of the lower member. Alternatively, the upper and lower yokes may be dimensioned to snugly compress the conduit 56 against the inner couplings of the nipples 62a and 62b. Care must be taken to avoid an uneven compression causing the conduit 56 to bind, providing a potential source of leakage.

The wall 26 is provided with a vertically projecting retainer wall 106 dimensioned to cooperate with a notch provided in the lower wall 30 of the lower member 24. The retainer wall 106 may be dimensioned to snugly circumferentially compress or collar the tubing 12 to the outer coupling 84 of the nipple 62a to assist in insuring fluid-tight integrity. A similar retaining wall and notch may be provided at the outlet end 18 of the clamp 10.

The yokes insure that the nipples 62a and 62b of conduit 56 are snugly captured within the retainer spaces 88 and 90. The conduit 56 is further captured within the body 20 by fitting the retainer rings 80 and 86 within the notches 92 and 94. The captured conduit is thereby unaffected by external forces such as pulling tugging or stretching of either tubing 12 or 18. Stretching of the conduit 56 would vary the flow lumen size and thereby undesirably affect the flow rate. Additionally, the walls 26, 30 and 28, 32 may be more vertically angled than is shown in FIG. 4 to reduce the size of spaces 88 and 90 and to more snugly secure the nipples within the retaining spaces if desired.

In a preferred form of the present invention, the length of conduit 56, provided with nipples 62a and 62b, or suitable securing means, is slightly shorter by a predetermined amount than the distance between the yokes. When the retaining rings are placed within the retaining spaces on either side of the yokes, the shorter conduit is slightly elongated or stretched by a pre-determined amount. We have found that this elongation optimizes flow rate stability and substantially prevents the conduit from binding or bunching together on the forward side during movement of the roller. We have found that a range of approximately 4 to 8 percent elongation of the conduit is optimum for flow rate stability and to alleviate bunching of the conduit.

The body 20 of the clamp 10 is preferably significantly longer compared to other roller clamp bodies to permit a gradual angular variance of the compression surface 70 to the path of the roller 50 along its track. The range of flow control sensitivity is thereby enhanced to provide a clamp which is accurately regulatable over small incremental changes in flow rate.

The clamp 10 of the present invention may be an integral part of a standard fluid administration set, such as a parenteral set, in which the conventional vinyl inlet and outlet tubes may be solvent bonded to the outer couplings of the fluid inlet and outlet. Additionally, the clamp may be employed with any fluid administration system by appropriately removing a length of tubing or severing the same and inserting the flow regulating clamp of the present invention. When it is desired to set a particular flow rate setting, the operator grips the clamp and longitudinally positions the roller within the passageway until the flow lumen of the conduit obtains an internal area corresponding to the desired flow rate.

The present invention is more readily assembled when the preferred two piece clam-shell like body 20 is employed. The conduit 56 having suitable clips or nipples 62a and 62b at both ends is readily inserted into appropriate retainer spaces in the lower member of the body 24, followed by insertion of the roller 50 and the assembly of the upper member 22 at the juncture 42 to the lower member 24. Numerous methods of bonding the upper and lower members together may be employed, such as, for example, solvent or heat bonding.

From the foregoing description of the specific structure of the preferred embodiments, it will be apparent to one skilled in the art that numerous modifications may be made without departing from the spirit of the invention, nor from the scope of the appended claims. All such modifications and alterations are intended to be included within the scope of the invention as defined by the appended claims.

What is claimed:

1. A roller clamp for regulating the rate of fluid flow from a supply source to a desired delivery point through plastic tubing comprising:

an elongated, box-like body having a base portion with an internal compression surface, a top portion with an elongated, open passageway, elongated side walls, and end walls;

a centrally disposed passageway in said end walls defined by a fluid inlet means at one end wall for receiving the plastic tubing from said supply source, and a fluid outlet at the opposite end wall for receiving the plastic tubing leading to the delivery point;

a length of conduit fabricated from silicone rubber having a lumen for the passage of fluid through the body from the inlet to the outlet, said conduit being disposed and captured within the body in stretched condition between said inlet and said outlet means so as not to be affected by external stretching and tugging forces;

a roller having a circumferential outer surface and centrally disposed axle hubs;

a track within the body for capturing said roller for longitudinal movement within said body, said compression surface having an angular variance to the track to provide a variable distance between the outer surface of the roller in contact with the conduit and the base;

whereby the fluid flow may be varied by application of a manual force to the roller, thereby altering the diameter of the lumen from fully open to completely closed as defined by the area between the roller and compression surface.

2. The roller clamp of claim 1 in which said body is longitudinally divided into two cooperating pieces including an upper member and a lower member.

3. The roller clamp according to claim 2 wherein the track further includes:

a roller bearing surface in the lower member adjacent and joined to the compression surface by a shoulder of varying height defining a variable area below the plane of the roller bearing surface; and axle hub bearing surfaces formed in the upper member and uniformly spaced above the roller bearing surfaces so that when said upper and lower body members are secured together the outer surface of the roller is maintained in slightly biased engagement with the roller bearing surface.

4. The roller clamp according to claims 1 or 3 wherein the fluid inlet means and fluid outlet means further includes:

a short, rigid coupling dimensioned to snugly hold the conduit in fluid-tight engagement to the coupling within the interior of the body;

a retainer of slightly larger diameter than the coupling; and means for securing the retainer within the body to internally trap the conduit therein so as to protect the conduit from external stretching and tugging forces.

5. The roller clamp according to claim 4 wherein the body and means for securing the retainer further includes:

a first set of projecting means within the body adjacent to the end walls defining a retainer space dimensioned so as to secure the retainer of the coupling in said space thereby preventing external forces from affecting the conduit.

* * * * *